United States Patent [19]

Andrews

[11] Patent Number: 5,306,711
[45] Date of Patent: Apr. 26, 1994

US005306711A

[54] ORGAN PRESERVATIVE SOLUTION

[75] Inventor: Peter Andrews, Falls Church, Va.

[73] Assignee: Georgetown University, Washington, D.C.

[21] Appl. No.: 903,477

[22] Filed: Jun. 24, 1992

[51] Int. Cl.$^5$ ............................................. A61K 31/715
[52] U.S. Cl. ...................................... 514/59; 514/832; 514/833; 435/1; 536/112; 600/36; 604/4
[58] Field of Search ................... 514/59, 60, 832, 833; 600/36; 604/4; 435/1; 536/112

[56] References Cited

U.S. PATENT DOCUMENTS

| | | | |
|---|---|---|---|
| 4,438,108 | 3/1984 | Sanders et al. | 514/56 |
| 4,452,818 | 6/1984 | Haidt | 514/915 |
| 4,740,594 | 4/1988 | Mauzac et al. | 514/59 |
| 4,798,824 | 1/1989 | Belzer et al. | 514/832 |
| 4,829,984 | 5/1989 | Gordon | 600/12 |
| 4,873,230 | 10/1989 | Belzer et al. | 514/60 |
| 4,879,283 | 11/1989 | Belzer et al. | 514/60 |
| 5,082,831 | 1/1992 | Leaf et al. | 514/56 |

OTHER PUBLICATIONS

"Optisol Corneal Storage Medium" by Kaufman et al., vol. 109, Jun. 1991, Arch Ophthalmol pp. 864-868.

"The Cornea" edited by Kaufman et al., pp. 717-720 (1988).

"Ultrastructure of Kidney Preservation: Varying the Amount of an Effective Osmotic Agent in Isotonic and Hypertonic Preservation Solutions" by Coffey & Andrews, pp. 136-143, vol. 35, No. 2 *Transplantation*.

"72-HR Canine Kidney Preservation Without Continuous Perfusion" by Ross, Marshall & Escott, vol. 21, No. 6, pp. 498-501, Jun. 1976 *Transplantation*.

"Effects of Preservation Conditions and Temperature on Tissue Acidification in Canine Kidneys" by Kallerhoff, Holscher, Kehrer, Glab, & Bretschneider, vol. 39, No. 5, pp. 485-489 *Transplantation*.

"Improved 72-Hour Renal Preservation with Phosphate-Buffered Sucrose", by Lam, Mavor, Potts, and Giles, vol. 47, No. 5, May 1989, pp. 767-771 *Transplantation*.

"Successful 72-Hour Cold Storage Kidney Preservation with UW Solution" by Ploeg, Goossens, Vreugdenhil, McAnulty, Southard and Belzer, vol. XX, No. 1, Suppl 1 (Feb.), 1988: pp. 935-938 *Transplantation Proceedings*.

"Factors that Improve the Preservation of Nephron Morphology During Cold Storage", vol. 46, No. 1 pp. 100-120, 1982 by Andrews, and Coffey *Laboratory Investigation*.

"Safe Preservation of Human Renal Cadaver Transplants by Euro-Collins Solution up to 50 Hours", vol. XIII, No. 1 (Mar.), 1981, pp. 693-696 *Transplantation Proceedings*.

"Tandem Scanning Confocal Microscopy (TSCM) of Normal and Ischemic Living Kidneys" by Andrews, Petroll, Cavanaugh, and Jester, The American Journal of Anatomy 191:95-102 (1991).

"Kidney Preservation for Transportation by Collins", The Lancet, Dec. 1969, pp. 1219-1222.

"Canine Kidney Preservation Using a New Perfusate" by Sacks, Petritsch and Kaufman, The Lancet, May 73, pp. 1024-1028.

*Primary Examiner*—Ronald W. Griffin
*Attorney, Agent, or Firm*—Oblon, Spivak, McClelland, Maier & Neustadt

[57] ABSTRACT

An organ preservative solution containing a low molecular weight dextran in a pharmacologically acceptable storage solution is suitable for storage and preservative of organs for transplantation.

25 Claims, No Drawings

ORGAN PRESERVATIVE SOLUTION

BACKGROUND OF THE INVENTION

1. Field of the Invention

The present invention is directed to a preservative solution suitable for preserving organs. More specifically, the invention is directed to an organ preservative solution containing a dextran having a molecular weight of 10,000 daltons or less which provides superior preservation properties.

2. Discussion of the Background

Organ transplantation has become a routine means of treating certain diseases of the organs. Transplantation requires a ready source of organs, such as kidney, pancreas, liver, heart, etc., from living persons or cadavers. Currently, most vital organs which are used for transplantation are obtained from heart beating cadavers and preserved for variable periods of time prior to their transplantation.

The two principal methods of preserving organs for transplantation are continuous pulsatile perfusion and simple hypothermic storage in a preservation solution. In pulsatile perfusion, the organ is subjected to pulsatile flow of a perfusate under hypothermic conditions such that the organ membranes receive sufficient oxygenation. Typically, the perfusate contains albumin and lipids.

With simple hypothermic storage, organs are removed from a cadaver donor and rapidly cooled. Rapid cooling is achieved by external cooling and by perfusion with a preservative solution to lower the internal temperature of the organ. The organ is then stored immersed in the preservative solution at temperatures of about 0°–4° C.

Significant medical advantages are achieved if organs for transplantation can be stored and preserved for 2–3 days and longer. Longer storage times provide additional time for histocapability testing of the donor and recipient, organ viability testing and provides additional time for preoperative decisions and preparations.

Numerous preservative solutions have been developed and used to preserve major organs while they are in cold storage prior to their transplantation. These preservative solutions contain a variety of compounds which act as osmotic agents to prevent cell swelling and thereby protect the organs from swelling associated cellular necrosis during storage. The degree of necrosis occurring in a stored organ can be observed by using conventional light microscopy with fixed tissue samples. More recently, the use of tandem scanning confocal microscopy (TSCM) has provided a noninvasive real time microscopic imaging technique for determining the degree of necrosis in organs (P. M. Andrews et al, Am. J. Anat., 1991, 191:95–102). Specific cell damage which can be observed includes extensive swelling and rupturing of cells and accumulation of cytoplasmic debris.

Two widely used preservative flush solutions which are commercially available are the Collins (G. M. Collins, The Lancet, 1969, 1219–1222) and the Euro-Collins (J. P. Squifflet et al, Transplant. Proc., 1981, 13:693–696) solutions. These solutions resemble intracellular fluid and contain glucose as an osmotic agent. Despite their widespread use, the Collins and Euro-Collins preservative solutions do not provide adequate preservation for storage times greater than about 48 hours. For example, kidneys stored in Collins solution for 24 hours exhibited considerable damage to the nephrons. This damage included degradation of cells lining the proximal tubules, extensive swelling and rupturing of cells lining the ascending distal tubules, degeneration of glomerular epithelial and endothelial cells and accumulation of flocculent cytoplasmic debris in the capsular spaces of Bowman. (P. M. Andrews et al, Lab. Invest., 1982, 46:100–120).

In addition to glucose, high osmolality preservative solutions have been prepared using raffinose and lactobionate as in the UW preservative solution (R. J. Ploeg et al, Transplant. Proc., 1988, 20 (suppl 1) 1:935–938), mannitol in the Sacks solution (S. A. Sacks, The Lancet, 1973, 1:1024–1028), sucrose in the phosphate buffered sucrose (PBS) preservative solution (F. T. Lam et al, Transplantation, 1989, 47:767–771) and the histidine buffered HTK solution of Bretschneider (N. M. Kallerhoff et al, Transplantation, 1985, 39:485–489). Hypertonic citrate preservative solutions are also known (H. Ross et al, Transplantation, 1976, 21:498–501). The effectiveness of these solutions as preservative solutions for organs appears to be related to the specific osmotic agent which is used (A. K. Coffey and P. M. Andrews, Transplantation, 1983, 35:136–143).

Preservative solutions are also known which contain synthetic hydroxyethyl starch (HES) as an osmotic colloid. The HES has an average molecular weight of about 150,000 to about 350,000 daltons and a degree of substitution of from about 0.4 to about 0.7. (See U.S. Pat. No. 4,879,283 and U.S. Pat. No. 15 4,798,824). U.S. Pat. No. 5,082,831 discloses a total body washout perfusion solution containing high molecular weight (500,000 daltons) hydroxyethyl starch. The HES washout solution produces substantially less edema than conventional washout solutions containing DEXTRAN 40 as a colloid. Solutions containing DEXTRAN 40 produce edema, particularly in the pancreas and lungs.

Preservative solutions are also known for preserving corneas for transplantation. Corneal preservative solutions are designed to prevent endothelial cell damage. Corneal preservative solutions containing glucose or dextran are known (H. E. Kaufman et al, Arch. Ophthalmol., 1991, 109:864–868; B. E. McCarey and H. E. Kaufman, 1974, Invest. Ophthalmol., 1974, 13:859; B. E. McCarey and H. E. Kaufman, Invest. Ophthamol., 1974, 13:165). The corneal preservative solutions known as OPTISOL, DEXSOL and MK contain DEXTRAN 40 (average molecular weight=40,000 daltons) as an osmotic agent at a concentration of 1–5 wt %. The compositions of these known solutions are shown in Table 1 below.

TABLE 1

| Constituents of Three Corneal Storage Media* | | | | |
|---|---|---|---|---|
| Constituent | OPTISOL | DEXSOL | MK | K-SOL |
| Base medium | Hybrid of TC-199 and MEM | MEM | TC-199 | TC-199 |
| Chondroitin sulfate, % | 2.5 | 1.35 | 0 | 2.5 |
| Dextran (molecular weight = 40,000 d, DEXTRAN T-40), % | 1 | 1 | 5 | 0 |
| HEPES buffer | Yes | Yes | Yes | Yes |
| Gentamicin sulfate | Yes | Yes | Yes | Yes |
| Nonessential amino acids, mmol/L | 0.1 | 0.1 | 0 | 0 |
| Sodium bicarbonate | Yes | Yes | Yes | Yes |
| Sodium pyruvate, mmol/L | 1 | 1 | 0 | 0 |
| Additional | Yes† | Yes | No | No |

TABLE 1-continued

| Constituents of Three Corneal Storage Media* | | | | |
|---|---|---|---|---|
| Constituent | OPTISOL | DEXSOL | MK | K-SOL |
| antioxidants | | | | |

*Mem indicates minimal essential medium; TC-199, tissue culture medium 199. OPTISOL and DEXSOL are manufactured by Chiron Ophthalmics, Inc., Irvine, Calif. K-SOL was manufactured by Cilco Inc., Huntington, Va. but is no longer commercially available.
†Proprietary information, Chiron Ophthalmics.

Although many organ preservative solutions are known, these known solutions do not provide adequate preserving properties, particularly at longer storage times. Accordingly, a need continues to exist for improved organ preservative solutions capable of preserving organs for longer periods of time, thereby facilitating transplantation of these organs.

SUMMARY OF THE INVENTION

Accordingly, one object of the present invention is to provide an organ preservative solution capable of improved organ preservation.

A further object of the invention is to provide a method for preserving organs using the novel preservative solution of the present invention.

These and other objects which will become apparent from the following specification have been achieved by the present organ preservative solution which contains a low molecular weight dextran osmotic agent. This preservative solution provides a method for preserving organs for extended periods of time using cold storage.

DETAILED DESCRIPTION OF THE PREFERRED EMBODIMENTS

It has now been discovered that the presence of a low molecular weight dextran in a pharmacologically acceptable organ storage solution provides a preservative solution having superior organ preserving properties relative to known preservative solutions. Organs stored in the solution of the present invention are in significantly better condition than when stored in conventional preservative solutions, i.e., organs stored in the preservative solution of the present invention exhibit less necrosis during storage. The preservative solution of the present invention, therefore, has wide utility as an organ preservative solution for preserving organs prior to transplantation.

The solution of the present invention may be utilized to preserve major organs such as the kidney, heart, pancreas, liver, lungs and intestines and portions or segments thereof. Organs are preserved by flushing the organ after it has been removed from a cadaver With the preservative solution of the present invention followed by cold storage of the organ in the preservative solution at temperatures of about 0°-4° C. Organs stored in the preservative solution can then be transplanted to an appropriate transplant recipient.

The preservative solution of the present invention is a pharmacologically acceptable solution such as an aqueous buffer solution, preferably an aqueous phosphate buffer solution, containing a dextran having an average molecular weight of 10,000 daltons or less. An aqueous phosphate buffer can be prepared, for example, by mixing sodium hydrogen phosphate ($Na_2HPO_4$) and sodium dihydrogen phosphate ($NaH_2PO_4$) in water. preferably, the water should be purified by distillation, deionization, etc. prior to use. If a cardioplegic solution for preservation of hearts is desired, a phosphate buffer solution can be prepared using potassium hydrogen phosphate ($K_2HPO_4$) and/or potassium dihydrogen phosphate ($KH_2PO_4$).

The low molecular weight dextran is added to the pharmacologically acceptable storage solution. The preservative solution should have a pH of 7.0 or greater; preferably in the range of 7.1-7.4, more preferably about 7.2-7.4, optimally about 7.2. Preservative solutions having a pH below 7.0 are not suitable for preserving organs and allow tissue necrosis.

A particularly preferred preservative solution contains 141 mmol/l sodium ions 79 mmol/l phosphate ions and 30 g/l dextran. This preferred embodiment can be prepared by adding 8.95 g $Na_2HPO_4$ and 2.16 g $NaH_2PO_4 \cdot H_2O$ to a liter of water together with 25-30 wt. % of the low molecular weight dextran to give a solution having a pH of 7.2-7.4.

When using a phosphate buffer, it has been discovered that the amount of sodium or potassium hydrogen phosphate and sodium or potassium dihydrogen phosphate required to produce a final preservative solution having the required pH is greater than the amount of these phosphates which is required to produce an aqueous phosphate buffer solution in the absence of the dextran. That is, it has been discovered that the presence of the dextran results in a decrease in pH of the preservative solution requiring additional amounts of sodium or potassium hydrogen phosphate and sodium or potassium dihydrogen phosphate to bring the pH of the final preservative solution to the desired range. The amount of additional sodium or potassium dihydrogen phosphate and sodium or potassium hydrogen phosphate which is required to form the preservative solution of the present invention in the presence of the dextran, can be determined by monitoring the pH of the preservative solution and adding the hydrogen phosphate and dihydrogen phosphate salts portionwise until the desired pH value has been obtained.

The low molecular weight dextran which is used in the preservative solution of the present invention has an average molecular weight of 10,000 daltons or less, preferably about 5,000-10,000 daltons, more preferably about 5,700-9,700 daltons. The low molecular weight dextran may obviously be a mixture of dextrans. Suitable dextrans are commercially available.

Dextrans having an average molecular weight greater than 10,000 daltons, such as DEXTRAN 40 (available from Pharmacia), used in the corneal preservative solutions OPTISOL, DEXSOL and MK are incapable of providing good preservation of organs at similar concentrations as shown in the examples below. Equal amounts of these higher molecular weight dextrans do not provide the cold storage preservation capability of the preservation solutions of the present invention which utilize low molecular weight dextrans. Solutions containing high molecular weight dextrans also have a higher viscosity and are therefore more difficult to handle and use.

The preservative solutions of the present invention may contain the low molecular weight dextran as the only osmotic agent or, if desired, may contain a mixture of the low molecular weight dextran and another osmotic agent. Suitable conventional osmotic agents include any osmotic agent known for use in preservative solutions, including mannitol, sucrose, raffinose, and lactobionate. When the low molecular dextran is used as the only osmotic agent, the preservative solution should contain about 20-30 wt. %, preferably 25-30 wt. % of the low molecular weight dextran to provide adequate osmolality and preservation properties. A portion of the low molecular dextran may be replaced with any osmotic agent in any amount so long as the preservative solution has sufficient osmolality to preserve the organ. Generally, a preservative solution having a mixture of the low molecular weight dextran and another osmotic agent should have the same osmolality as a preservative solution containing 20-30 wt. % of the low molecular weight dextran as the only osmotic agent. Preferably, 5-95 wt. %, more preferably 10-50 wt. % of the low molecular weight dextran is replaced with another osmotic agent to provide the preservative solutions of the present invention.

Organs stored in the preservative solution of the present invention demonstrate significantly less necrosis during cold storage when compared with other preservative solutions. This significantly lesser degree of necrosis can be confirmed by observation of living cold stored organs using the recently developed techniques of vital microscopy (TSCM) as well as observations of fixed samples using traditional light and electron microscopy.

If desired, the preservative solution of the present invention may contain other components which do not adversely affect the preservative properties of the solution. For example, addition of glutathione or a $C_{1-6}$ alkyl glutathione monoester (M. E. Anderson et al, Arch. Biochem. Biophys., 1985, 239:538-548, ethyl ester)in amounts of about 2-10 mmol/l, preferably about 4-8 mmol/l, optimally about 6 mmol/l to the preservative solution are useful in preventing reflow damage following transplantation of the cold preserved organ.

Other features of the invention will become apparent in the course of the following descriptions of exemplary embodiments which are given for illustration of the invention and are not intended to be limiting thereof.

EXAMPLES

In the experiments described below, a well established rat model for evaluating the degree of necrosis suffered by kidneys during their cold storage prior to transplantation was used to evaluate the preservative solution of the present invention (P. M. Andrews and A. K. Coffey, Lab. Invest., 1982, 46:100-120; A. K. Coffey and P. M. Andrews, Transplantation, 1983, 35:136-143). This model involves vascular perfusion of the kidneys in vivo with the cold preservative solution, vascular perfusion fixation of the kidneys after selected periods of cold storage (with phosphate buffered 2.5% glutaraldehyde) and microscopic evaluation of the kidney parenchyma.

In the experiments described below, the degree of necrosis exhibited over 3, 4 and 5 days of cold storage in the preservative solution of the present invention was determined as compared with cold storage for identical time periods in Euro-Collins and UW preservative solutions. The degree of necrosis exhibited by different segments of the nephron was determined by conventional light microscopy and by vital microscopy using TSCM to observe living kidneys over time, i.e., every 24 hours, while the living kidney was preserved in each of the preservative solutions.

The preservative solution of the present invention used in the experiments described below is an aqueous phosphate buffer solution containing 30 grams/liter DEXTRAN T-10 ® (Pharmacia). The composition of this solution of the present invention (DEX) is compared with the compositions of Euro-Collins (EC) and UW preservative solutions in Table 2 below. For comparison, the compositions of Collins, Sacks No. 1, Sacks No. 2, hypertonic citrate (HOC), phosphate buffered sucrose (PBS) and HTK preservative solutions are also shown in Table.

TABLE 2

| Inorganic Components (mmol/Liter) | Collins | Sacks No. 1 | Sacks No. 2 | HOC | EC | UW | PBS | DEX | HTK |
|---|---|---|---|---|---|---|---|---|---|
| Sodium | 10 | 10 | 14 | 80 | 10 | — | 120 | 141 | 15 |
| Potassium | 115 | 115 | 126 | 80 | 115 | 25 | — | — | 10 |
| Magnesium | 30 | — | 8 | 35 | — | 5 | — | — | 4 |
| Chloride | 15 | 16 | 16 | — | 15 | — | — | — | 50 |
| Bicarbonate | 10 | 20 | 20 | — | 10 | — | — | — | — |
| Citrate | — | — | — | 55 | — | — | — | — | — |
| Sulfate | 30 | — | — | 35 | — | 5 | — | — | — |
| Phosphate | 50 | 50 | 60 | — | 50 | 25 | 60 | 79 | — |
| Impermeants (Grams/Liter) | | | | | | | | | |
| Glucose | 25 | — | — | — | 35 | — | — | — | — |
| Mannitol | — | 50 | 37.5 | 34 | — | — | — | — | — |
| Sucrose | — | — | — | — | — | — | 47.9 | — | 30 |
| Raffinose | — | — | — | — | — | 17.83 | — | — | — |
| Hydroxyethyl starch | — | — | — | — | — | 50 | — | — | — |
| Lactobionate | — | — | — | — | — | 35.83 | — | — | — |
| DEXTRAN T-10* | — | — | — | — | — | — | — | 30 | — |
| Metabolites and others | | | | | | | | | |
| Adenosine (mmol/Liter) | — | — | — | — | — | 5 | — | — | — |
| Glutathione (mmol/Liter) | — | — | — | — | — | 3 | — | — | — |
| Allopurinol (mmol/Liter) | — | — | — | — | — | 1 | — | — | — |
| Insulin (U/Liter) | — | — | — | — | — | 100 | — | — | — |
| Dexamethasone (mg/Liter) | — | — | — | — | — | 8 | — | — | — |
| Heparin (1 U/Liter) | 5,000 | — | — | — | — | — | — | — | — |
| Procaine (Grams/Liter) | 0.10 | — | — | — | — | — | — | — | — |
| Tryptophan (mmol/Liter) | — | — | — | — | — | — | — | — | 2 |
| Ketoglutarate (mmol/Liter) | — | — | — | — | — | — | — | — | 1 |
| Histidine/histidine-HCL (mmol/Liter) | — | — | — | — | — | — | — | — | 180/18 |

*Molecular Weight of between 5,000 and 10,000

EXAMPLE 1

Experiments Using Traditional Light Microscopy Comparing the Cold Storage of Kidneys in Euro-Collins Solution, UW Solution and DEX Solution Adult rat kidneys were perfused in vivo with Euro-Collins Solution, UW solution and DEX solution of the present invention and stored for 3, 4 or 5 days. A minimum of 9 kidneys were evaluated for each storage solution. Following storage, the kidneys were fixed and evaluated using an Olympus BH2 light microscope and scored on a scale of 0–4, with 0 indicating no necrosis and 4 indicating total necrosis. The kidneys stored in Euro-Collins solution exhibited total necrosis of most of the cortical uriniferous tubules following 3 days of cold storage. The kidneys stored in the UW solution exhibited somewhat less necrosis, but still exhibited major necrosis of most of the cortical uriniferous tubules following 3 days of storage. The kidneys stored in the DEX preservative solution of the present invention exhibited no significant necrosis, even after 5 days of cold storage. The preservative solution of the present invention provides significantly longer preservative periods with less necrosis than the Euro-Collins or UW solutions.

EXAMPLE 2

Experiments Using Tandem Scanning Confocal Microscopy to Evaluate Tubular Necrosis of the Living Kidneys During Cold Storage Tandem Scanning Confocal Microscopy (TSCM) is a relatively new form of vital microscopy which is capable of evaluating the status of superficial nephrons, i.e., the uriniferous tubules and glomeruli adjacent to the kidney capsule, in living kidneys without undergoing the need for tissue fixation, embedding, and sectioning. In this study, kidneys were again perfused in vivo with either cold Euro-Collins solution, UW solution or the DEX solution of the present invention. Every 24 hours during cold storage, the superficial nephrons were viewed by TSCM and their status recorded on video tape. At least six kidneys were evaluated using each of the three preservative solutions. This study revealed that the superficial tubules in the cold stored kidneys were the first uriniferous tubules to undergo necrosis during cold storage and thereby provided a sensitive indicator of the status of cold stored kidneys. Following 24 hours of cold storage, the superficial tubules of kidneys stored in Euro-Collins solution exhibited significant necrosis. Following 48 hours, the superficial tubules of kidneys stored in the UW solution also exhibited significant necrosis. It was only following 72 hours of cold storage that kidneys stored in the DEX solution of the present invention began to exhibit necrosis.

It may be concluded that TSCM of living kidneys confirms the conventional light microscopic observations of fixed kidneys indicating that the solution of the invention is superior to both the Euro-Collins and UW preservative solutions in reducing the degree of tubular necrosis during cold storage.

EXAMPLE 3

Experiments to Determine the Optimal Amount of Low Molecular Weight Dextran to add to the Preservative Solution in Order to Obtain the Best Degree of Organ Preservative Kidneys were perfused in vivo with cold preservative solutions made up in the same manner except that one preservative solution contained 10 wt. % low molecular weight dextran (DEXTRAN T-10), a second contained 15 wt. % dextran, a third contained 20 wt. % dextran, a fourth contained 25 wt. % dextran, and a fifth contained 30 wt. % dextran. Following storage for five days in one of the foregoing solutions, all the kidneys were fixed by vascular perfusion and prepared for and evaluated by conventional light microscopy as described above. The results revealed that there was a significant degree of necrosis of the kidneys stored in both the 10 wt. % and the 15 wt. % dextran solutions. Very little necrosis was exhibited by the kidneys stored in solutions containing 20 wt. %, 25 wt.%, or 30 wt.% dextran.

EXAMPLE 4

Experiments to Compare the Ability of Low Molecular Weight Dextran to Preserve Kidneys with Dextrans of Higher Molecular Weight.

Kidneys were perfused in vivo with preservative solutions made up in the same manner except that one contained 25 wt. % low molecular weight dextran (DEXTRAN T-10) while the other contained 25 wt. % DEXTRAN T-40 (Pharmacia; average molecular weight 40,000 daltons). All kidneys were stored for four days, fixed by vascular perfusion, and evaluated by conventional light microscopy as described above. Three kidneys were evaluated in each group. The kidneys stored in DEXTRAN T-40 exhibited significant necrosis of the cortical uriniferous tubules. The kidneys stored in DEXTRAN T-10, however, exhibited no necrosis of these same tubules. It may be concluded that dextran having an average molecular weight of 40,000 does not provide the superior preservative solution which is otherwise provided by the solution of the present invention.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An organ preservative solution, comprising a pharmacologically acceptable storage solution and 20–30 wt % dextran having an average molecular weight of 10,000 daltons or less, said preservative solution having a pH of 7.0 or greater.

2. The solution of claim 1, having a pH of 7.1–7.4.

3. The solution of claim 2, having a pH of 7.2–7.4.

4. The solution of claim 1, wherein said dextran has an average molecular weight of about 5,000–10,000 daltons.

5. The solution of claim 4, wherein said dextran has an average molecular weight of about 5,700–9,700 daltons.

6. The solution of claim 1, further comprising 2–10 mmol/l glutathione of a $C_{1-6}$ alkyl glutathione monoester.

7. The solution of claim 6, comprising 4–8 mmol/l glutathione or a $C_{1-6}$ alkyl glutathione monoester.

8. The solution of claim 1, comprising 25–30 wt. % of said dextran.

9. The solution of claim 1, wherein said storage solution is an aqueous phosphate buffer solution.

10. The solution of claim 9, wherein said preservation solution has a pH of 7.1–7.4 and said dextran has an average molecular weight of about 5,700–9,700 daltons.

11. The solution of claim 10, wherein 10–50 wt % of said dextran is replaced with sucrose.

12. The solution of claim 1, wherein 10–50 wt % of said dextran is replaced with a non-dextran osmotic agent.

13. A method of preserving an organ for transplantation, comprising submerging and storing the organ in a preservation solution comprising a pharmacologically acceptable storage solution and 20–30 wt % dextran having an average molecular weight of 10,000 daltons or less, said solution having a pH of 7.0 or greater.

14. The method of claim 13, wherein said organ is submerged and stored in said solution at a temperature of 0°–4° C.

15. The method of claim 13, wherein said preservative solution has a pH of 7.1–7.4.

16. The method of claim 15, wherein said preservative solution has a pH of 7.2–7.4.

17. The method of claim 13, wherein said dextran has an average molecular weight of about 5,000–10,000 daltons.

18. The method of claim 17, wherein said dextran has an average molecular weight of about 5,700–9,700 daltons.

19. The method of claim 13, wherein said preservative solution further comprises 2–10 mmol/l glutathione or a $C_{1-6}$ alkyl glutathione monoester.

20. The method of claim 19, wherein said preservative solution comprises 4–8 mmol/l glutathione or a $C_{1-6}$ alkyl glutathione monoester.

21. The method of claim 13, wherein said preservative solution comprises 25–30 wt. % of said dextran.

22. The method of claim 13, wherein said storage solution is an aqueous phosphate buffer solution.

23. The method of claim 22, wherein said preservation solution has a pH of 7.1–7.4 and said dextran has an average molecular weight of 5,700–9,700 daltons.

24. The method of claim 23, wherein 10–50 wt % of said dextran is replaced with sucrose.

25. The method of claim 13, wherein 10–50 wt % of said dextran is replaced with a non-dextran osmotic agent.

* * * * *